United States Patent
Lee

(10) Patent No.: US 7,112,062 B2
(45) Date of Patent: Sep. 26, 2006

(54) DENTAL MATERIAL STORAGE AND DELIVERY SYSTEM AND METHOD

(75) Inventor: Robert Lee, Lake Elmo, MN (US)

(73) Assignee: 3M Innovative Properties Co., St. Paul, MN (US)

(*) Notice: Subject to any disclaimer, the term of this patent is extended or adjusted under 35 U.S.C. 154(b) by 241 days.

(21) Appl. No.: 10/729,221

(22) Filed: Dec. 5, 2003

(65) Prior Publication Data

US 2005/0123878 A1   Jun. 9, 2005

(51) Int. Cl.
*A61C 5/04* (2006.01)

(52) U.S. Cl. .................. 433/89; 433/80; 206/63.5; 401/126

(58) Field of Classification Search ............ 433/80, 433/89; 401/126; 206/63.5
See application file for complete search history.

(56) References Cited

U.S. PATENT DOCUMENTS

| | | | |
|---|---|---|---|
| 5,848,894 A | 12/1998 | Rogers | |
| D403,768 S | 1/1999 | Mark et al. | |
| 5,860,806 A | 1/1999 | Pranitis, Jr. et al. | |
| D439,010 S | 3/2001 | Sogaro | |
| 6,413,087 B1 | 7/2002 | Petrich et al. | |
| 6,419,414 B1 | 7/2002 | Broyles et al. | |
| 6,592,280 B1 * | 7/2003 | Petrich et al. | 401/126 |
| 6,676,320 B1 * | 1/2004 | Wainer | 401/122 |
| 6,773,187 B1 * | 8/2004 | Gueret | 401/130 |
| 2001/0019680 A1 * | 9/2001 | Pieper et al. | 401/129 |
| 2002/0154935 A1 | 10/2002 | Petrich et al. | |

FOREIGN PATENT DOCUMENTS

EP   1 121 905 A2   8/2000

* cited by examiner

Primary Examiner—Ralph A. Lewis
Assistant Examiner—Casey Donahoe
(74) Attorney, Agent, or Firm—Sean J. Edman

(57) ABSTRACT

A dental material delivery system includes an applicator having a proximal segment, a median bending segment and a tip; an elongated handle; and a cap. The proximal segment of the applicator is nonremovably frictionally mounted within a proximal bore section of the handle, the median bending segment of the applicator is aligned generally longitudinally with an annular weakened wall line of the handle, and the tip of the applicator extends into a distal bore section of the handle. A quantity of dental material is disposed within the distal section of the handle. The cap is mounted to the handle adjacent the distal end of the handle to seal the handle. The wall of the handle is separable at the annular weakened wall line to permit withdrawal of the applicator tip and transfer of the dental material to a surface.

25 Claims, 3 Drawing Sheets

DENTAL MATERIAL STORAGE AND DELIVERY SYSTEM AND METHOD

BACKGROUND OF THE INVENTION

This invention relates to a unit dose dispenser (i.e., delivery system) that includes an applicator for applying a composition to a surface. The invention also relates to a method for forming the dispenser.

Applicators for applying compositions to surfaces are in widespread use in a variety of medical, commercial and household applications. Typical examples of such applicators include brushes and swabs having an overall stick-like configuration. Applicators that are relatively inexpensive represent a significant convenience to the user, in that the applicator can be disposed of after a single use.

In some instances, disposable applicators are individually packaged in closed, sealed containers. Individually packaged applicators are an advantage in medical and dental operations because sterility of the applicator can be assured until such time as the applicator is removed from the package in preparation for use. Examples of known packaged applicators include swabs that are contained between two sheets of a plastic or paper film, and swabs that are contained within a plastic tube or casing.

In some procedures, the composition to be applied by the applicator is provided in bulk containers. In those instances, the users may elect to dip the swab or brush tip of the applicator directly into the container in order to coat the tip with a small quantity of the composition. The tip is then removed from the container and moved across the desired surface in order to transfer the composition from the tip to the surface.

However, the practice of dipping the applicator tip directly into a bulk container is not satisfactory in many medical and dental applications due to the possibility of cross-contamination between patients. For example, if the applicator is used in a dental procedure to apply an adhesive to the surface of tooth structure, the practitioner may unknowingly transfer infectious disease from one patient to another if the applicator is returned to the bulk container after initial use in the oral cavity. The issue of cross-contamination can be avoided by using a new applicator in those instances where additional composition is needed, but such practice represents an additional expense and also requires a certain amount of time for retrieving, opening and preparing a new packaged applicator for use.

The problems of cross-contamination as mentioned above can be avoided by use of a dispensing well or pad. For example, in dental procedures a small quantity of composition is dispensed from the bulk container onto the well or pad, and the tip of the applicator is then used to transfer the composition from the well or pad to the patient's tooth structure. Such practice avoids the need for returning the applicator to the bulk container so that issues of cross-contamination between patients can be avoided. Once the procedure has been completed, the well or pad is disposed of or cleaned for reuse.

In recent years, there has been increased interest in packaged, disposable applicators having a tip that is pre-supplied with a quantity of a composition. These prepackaged applicators are a significant advantage in that the time that would otherwise be associated with handling of a bulk container and a disposing well or pad can be avoided. Moreover, such packaged applicators are a particular advantage when used with compositions that are messy or that are considered hazardous. Current single dose applicator assemblies are of a single size and only permit a specific quantity of composition to be pre-supplied to the applicator tip. However, not all procedures require the same amount of composition, and tip lengths and tip materials of the applicator for various procedures can vary.

Furthermore, in packaged applicator assemblies including a handle, applicator and receptacle portion, the applicator is typically removable from the handle to interchange applicators for various procedures. However, practitioners desire a single dose delivery system whereby an applicator removable from the handle is not desired to prevent problems with attaching the applicator or the applicator falling out of the handle.

One example of a packaged applicator assembly is described in U.S. Pat. No. 6,413,087 and includes an applicator having a tip that is pre-supplied with a single dose quantity of composition material. The applicator includes a cap initially extending over the tip and detachably connected to the applicator. The applicator includes a flexible portion that can be bent as the cap is detached from the applicator.

There is still a need to protect the packaged, disposable applicator and container from moisture and other contaminants. Thus, the packaged applicator and container are individually wrapped in a foil pouch for storage to protect the applicator and container and extend the shelf-life of the assembly. However, the foil pouch, or other suitable packaging increases the cost of the assembly.

Although a variety of applicators and application methods are known in the art, there exists a need for an improved applicator such that manufacture, use and storage of applicators and containers are enhanced. Such improvements should facilitate handling of the applicator, dispensing of the composition and result in manufacture ease without increasing the overall cost of the assembly or resulting in contamination of the composition.

BRIEF SUMMARY OF THE INVENTION

The present invention is directed to a method of forming a dental material storage container and dispenser (i.e., a dental material delivery system or applicator assembly). The method includes molding an elongated handle and a dental material applicator tip, engaging the tip to the handle, introducing a desired amount of dental material to the assembly and sealing the assembly to retain the dental material within the assembly. The handle may be molded of a cyclic olefin copolymer. The handle includes a length having a proximal closed end and a distal open end with a bore extending therein from the distal open end. The handle bore includes a tip retention section adjacent a proximal end thereof, with the handle having an annular weakened wall line along or distally from the tip retention section.

The dental material applicator tip is molded to have a proximal mounting segment, a median bending segment and a distal applicator segment. The proximal segment has a plurality of projections radially projecting therefrom and is formed to be received within the tip retention section of the handle bore. The proximal segment of the applicator tip is inserted into the tip retention section of the bore wherein the projections on the tip frictionally engage the bore to nonremovably fixedly connect the tip to the handle. The median bending segment of the tip is aligned with or distally from the radially extending weakened wall line of the handle.

A desired amount of dental material is introduced into the handle bore. A cap is aligned over the distal open end of the handle and the cap is sealed to the handle to retain the dental material in the bore. The cap may be formed from cyclic olefin copolymer.

The present invention is also directed to a dental material delivery system. The dental material delivery system includes an applicator having a proximal segment, a median bending segment and a distal tip segment. An elongated handle has a proximal end and a distal end; the handle having a generally cylindrical bore extending proximally therefrom from the distal end within a surrounding wall of the handle. The bore has a proximal section and a distal section. The handle wall includes an annular weakened wall line disposed generally between the proximal and distal sections of the bore. The proximal segment of the applicator is nonremoveably frictionally mounted within the proximal section of the bore, the median bending segment of the applicator is aligned generally longitudinally with the annular weakened wall line, and the distal tip segment of the applicator extends into the distal section of the bore.

A desired amount of dental material disposed within the distal section of the bore. A cap is mounted to the handle adjacent the distal end thereof to seal off the distal section of the bore. The wall of the handle is separable at the annular weakened wall line to permit withdrawal of the distal tip segment of the applicator from the distal section of the bore and transfer of dental material borne by the distal tip segment from the bore to a patient's dental anatomy.

BRIEF DESCRIPTION OF THE DRAWINGS

The present invention will be further explained with reference to the attached figures, wherein like structure is referred to by like numerals throughout the several views.

While the above-identified drawing figures set forth several embodiments of the invention, other embodiments are also contemplated, as noted in the discussion. In all cases, this disclosure presents the present invention by way of representation and not limitation. It should be understood that numerous other modifications and embodiments can be devised by those skilled in the art which fall within the scope and spirit of the principles of this invention.

DETAILED DESCRIPTION

Figure 1:
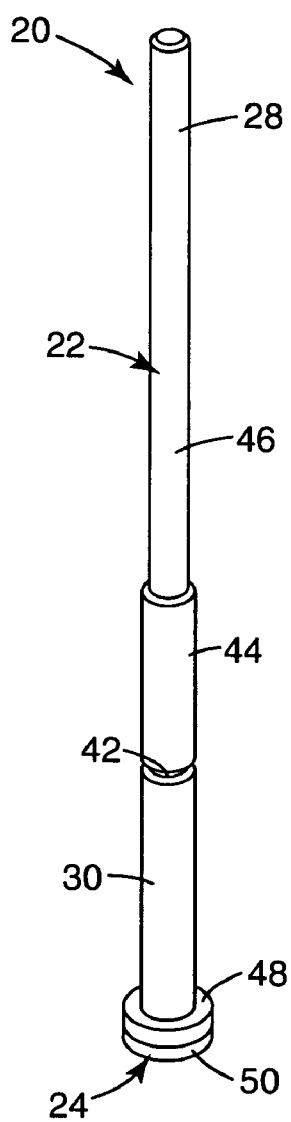
FIG. 1 is a perspective view of the present invention dental material delivery system.
Figure 2:
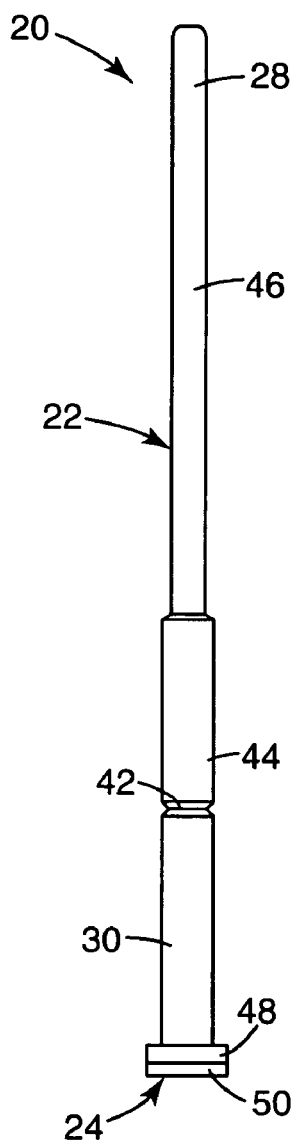
FIG. 2 is a side view of the dental material delivery system.
Figure 3:
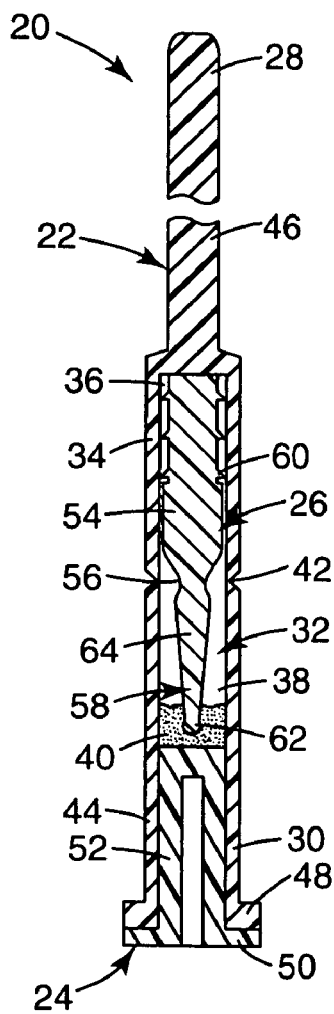
FIG. 3 is a cross-sectional view of the dental material delivery system.

FIGS. 1 and 2 are perspective and side views, respectively, of an applicator assembly 20, or dental material delivery system (e.g., a dental material container and dispenser). The assembly 20 stores a single unit dose of dental, pharmaceutical, medical or other material for transfer to a suitable surface, and the assembly 20 also includes an integral applicator and dispenser. FIG. 3 is a cross-sectional view of the assembly 20.

Figure 5:
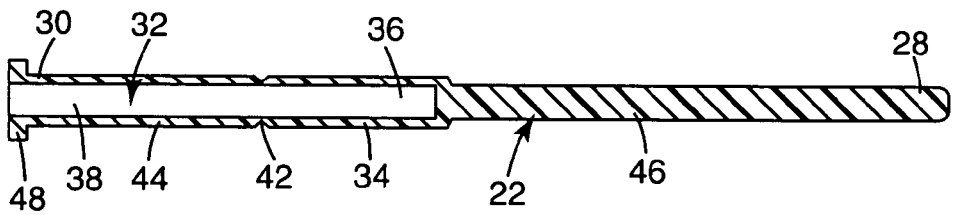
FIG. 5 is a cross-sectional view of a handle of the dental material delivery system.

The applicator assembly 20 includes an outer, elongated handle 22, a cap 24 and an applicator 26. The handle 22 includes a proximal closed end 28, a distal open end 30 and a generally cylindrical bore 32 extending proximally from the distal open end 30 within a surrounding wall 34 of the handle. The bore 32 includes a proximal tip retention section 36 and a distal section 38. A desired quantity of a composition material 40 is disposed withing the distal bore section 38, typically an amount sufficient to satisfy a single unit dose. The handle wall 34 has an annular weakened wall line 42 positioned between the proximal end 28 and the distal end 30 of the handle 22, and more particularly, disposed generally between the proximal and distal sections 36, 38 of the bore 32. FIG. 5 is a cross-sectional view of the handle 22, which further illustrates the handle.

The elongated handle 22 has a generally cylindrical shape with at least two different outer diameter portions, a first distal portion 44 and a second proximal portion 46 (as shown in FIG. 5). The first distal portion 44 extends distally from adjacent the proximal bore section 36 and has a first outer diameter. The second proximal portion 46 extends proximally from adjacent the proximal bore section 36 and has a second, smaller outer diameter. In addition, the handle 22 includes a radial extension 48 adjacent the distal end 30.

The cap 24 of the assembly 20 is mounted to the distal open end 30 of the handle 22 to seal off the distal bore section 38. The cap 24 is sized to fit within the distal bore section 38 at the distal end 30 of the handle 22. The cap 24 is sealed to the handle 22 to retain the composition material 40 within the distal bore section 38 and to create a hermetic seal. Some examples of sealing the cap 24 to the handle 22 are ultrasonic sealing and welding.

Figure 6A:
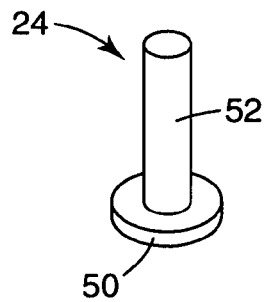
FIG. 6A is a perspective view of a cap for the present invention.
Figure 6B:
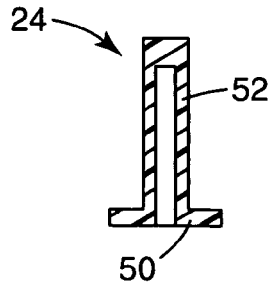
FIG. 6B is a cross-sectional view of the cap.

The cap 24 includes a radial extension 50, which abuts the radial extension 48 of the handle 22, and a longitudinal extension 52, also shown in FIGS. 6A and 6B. The longitudinal extension 52 of the cap 24 extends proximally from the distal open end 30 of the handle 22 into the distal section 38 of the bore 32. The longitudinal extension 52 of the cap 24 can be solid or hollow. The length of the longitudinal extension 52 determines an available volume of the distal bore section 38 for dental material 40, i.e., the available volume of the distal bore section 38 for dental material 40 is a function of the longitudinal extent of the longitudinal extension 52 of the cap 24. The available volume for dental material 40 is about 100 microliters to about 500 microliters.

Figure 7A:
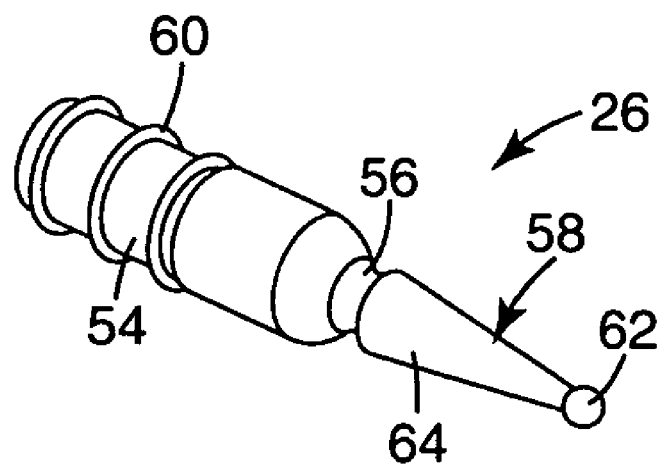
FIG. 7A is a perspective view of the applicator of the present invention.
Figure 7B:
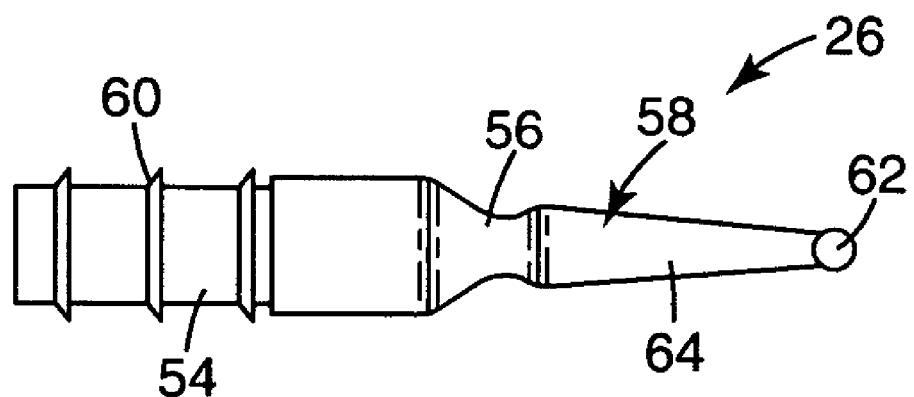
FIG. 7B is a side view of the applicator.

The applicator 26 of the assembly 20 includes a proximal mounting segment 54, a median bending segment 56 and a distal tip segment 58. FIGS. 7A and 7B further illustrate the applicator 26. The proximal segment 54 of the applicator 26 is nonremovably frictionally mounted within the proximal tip retention section 36 of the bore 32 (shown in FIG. 3). The proximal segment 54 of the applicator 26 includes a plurality of radial projections 60 thereon and radially projection therefrom. Some examples of the radial projections 60 include an annular directional ribbing, a ring, a flange, or a triangular extension.

The radial projections 60 are sized to form an interference fit with an inner diameter of the proximal section 36 of the bore 32, i.e., the inner surface of handle wall 34. The outer diameter of the proximal segment 54 of the applicator 26, including the radial projections 60, is about 3.0 millimeters (mm) to about 4.0 mm. The inner diameter of the proximal section 36 of the bore 32 is about 0 mm to about 0.2 mm larger than the outer diameter of the proximal segment 54, thereby facilitating an interference fit between the radial projections 60 and the handle 22. The proximal segment 54 of the applicator 26 is mounted within the bore 32 whereby flow of the dental material 40 proximally past the applicator 26 into the proximal section 36 of the bore 32 is prevented.

Figure 4:
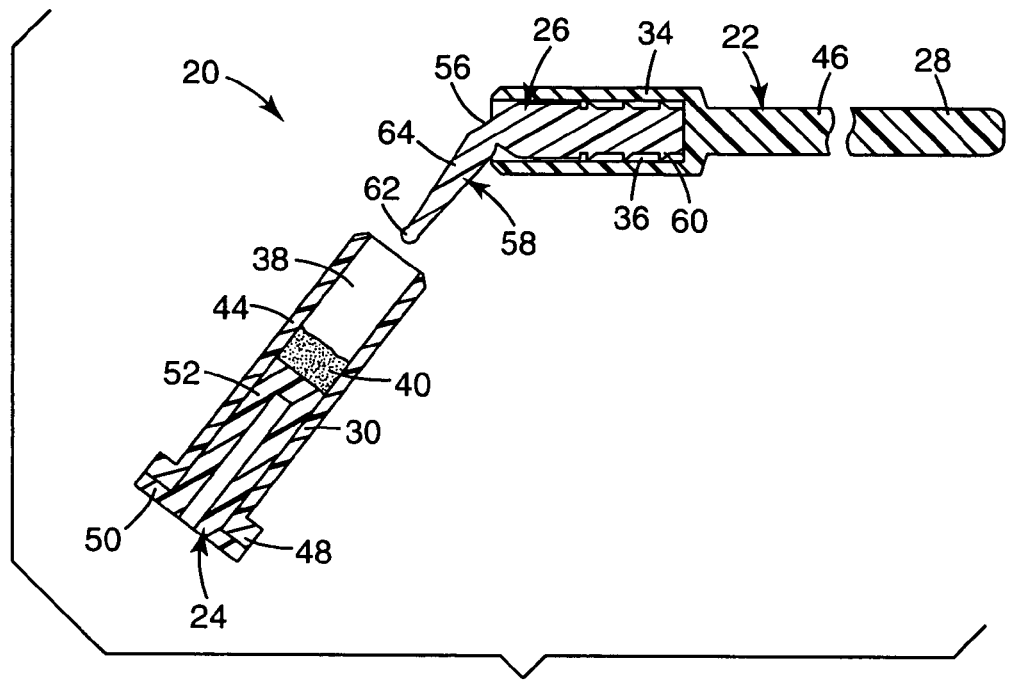
FIG. 4 is a cross-sectional view of the dental material delivery system separated to permit access to a dental material applicator.

The applicator 26 includes the median bending segment 56 located between the proximal mounting segment 54 and the distal tip segment 58. The proximal segment 54 of the applicator 26 is mounted within the proximal section 36 of the bore 32 such that the median bending segment 56 of the applicator 26 is aligned generally longitudinally with the annular weakened wall line 42 of the handle 22. The median bending segment 56 is deformable by finger pressure past its yield point to any one of a number of angular orientations (as shown in FIG. 4), and once bent will substantially self-remain in a bent orientation without returning to its initially straight orientation. Although some amount of return to its initially straight position is possible, it is preferred that the median bending segment 56 remains in approximately the same angular orientation to which it is bent after the bending pressure is released.

In the example shown in FIG. 3, the median bending segment 56 includes a single groove that circumscribes the applicator 26. The groove lies in a reference plane that is oriented perpendicular to the longitudinal axis of the assembly 20. Other constructions of the median bending segment 56 are possible, including a series of grooves, a section of reduced cross-sectional area of another shape, a weakened wall or an articulated joint to facilitate bending of the applicator. The distal tip segment 58 of the applicator 26 includes a tip 62 and an intermediate portion 64 positioned between the median bending segment 56 and the tip 62. The applicator 26 has a length of about 10 mm to about 40 mm, and the distal tip section 58 has a length of about 5 mm to about 15 mm. The proximal segment 54 of the applicator 26 is mounted within the proximal section 36 of the bore 32 such that the distal tip segment 58 extends into the distal section 38 of the bore 32, and more particularly, so that the tip 62 is deposited in the composition material 40. In the embodiment shown in FIG. 3, the intermediate portion 64 of the distal tip segment 58 is tapered and has a generally conical configuration. The tapered portion advantageously provides clearance in areas adjacent the tip 62 when used in certain applications. For example, if the tip 62 is used to apply a dental composition to overhanging tooth surfaces, the tapered portion facilitates application of the composition material in areas beneath that overhanging surface.

The tip 62 of the distal segment 58 of the applicator 26 has a generally spherical configuration, although other shapes are possible. Preferably, but not necessarily, the tip 62 includes a material that facilitates spreading of the composition material across the surface to which the composition material is to be applied. The tip material may be of any suitable structure that is compatible with the composition material and functions to distribute the composition over the receiving surface. Suitable materials include small bristles or fibers that serve as a brush and that are applied to all or only part of the tip.

Optionally, fibers can be applied to the tip 62 by a flocking process carried out by any technique known in the art. The flocked fibers define small interstitial spaces that can advantageously fill with the composition material, and retain and suspend a small amount of the composition material for efficient application to the surface of interest. The fibers also allow relatively uniform application of the composition in the same way as a brush would. If used in a dental procedure, the outwardly extending fibers permit the composition to be applied easily to side and overhanging surfaces of a tooth cavity as well as to the bottom of the tooth cavity.

Alternatively, other types of material may be applied to the tip 62 for facilitating spreading of the composition material across a surface. Examples of such other suitable materials include an open cell foam material such as polyurethane foam or synthetic sponge. Additional examples of suitable materials include woven and non-woven fabrics, gauzes and the like. Micro-structured surfaces could also be employed, including surfaces that are integrally formed as part of the tip 62.

The distal bore section 38 of the handle 22 defines a cavity that surrounds the distal tip segment 58, including the tip 62. The distal bore section 38 provides a reservoir for composition material 40 to be dispensed and applied by the tip 62. Optionally, the reservoir includes a porous material (not shown) that facilitates retention of the composition material 40 in the distal bore section 38 so that the composition material 40 does not drip from the bore 32 if the distal end 30 of the handle 22 is inverted after it is detached from the proximal end 28 of the handle 22.

Preferably, the optional porous material has suitable dimensions and is located in the distal bore section 38 such that the tip 62 slightly compresses the porous material. Such construction ensures that the tip 62 will remain wetted with the composition material 40. If additional composition material is needed once the composition material 40 on the tip has been exhausted, the tip 62 can be re-inserted into the distal bore section 38 of the handle 22 in order to contact the porous material or composition material and transfer more composition material to the tip 62.

FIG. 4 is a cross-sectional view of the applicator assembly 20 in which the distal end 30 of the handle 22 is separated from the proximal end 28 of the handle 22 to permit access to applicator 26 for transfer of the composition material 40 to a desired surface. The handle 22 is separable at the weakened wall line 42 (shown in FIG. 3) to permit withdrawal of the applicator 26 from the distal bore section 38. Annular weakened wall line 42 of the handle 22 separates the proximal end 28 from the distal end 30. Wall line 42 circumscribes the handle 22 in a region overlying the median bending segment 56 of the applicator 26. In one embodiment, the wall line 42 is a frangible area of reduced cross-sectional thickness that initially integrally interconnects the proximal and distal ends 28, 30 of the handle 22.

In use, the applicator assembly 20 is grasped by a user with one hand on the proximal end 28 of the handle 22 and the other hand on the distal end 30. The distal end 30 of the handle 22 extends a sufficient distance from the weakened wall line 42 to facilitate gripping of the distal end 30 for bending the distal end 30 with respect to the proximal end 28, and thereby separating the handle 22. Next, the proximal end 28 of the handle 22 (including the proximal mounting segment 54 of the applicator 26) and the distal end 30 of the handle 22 (including the distal tip segment 58 of the applicator 26) are moved in an arc such that the longitudinal axis of the proximal end 28 moves from a position collinear with the longitudinal axis of the distal end 30 to an orientation at a non-zero angle relative to the longitudinal axis of the distal end 30.

During the bending movement, the weakened wall line 42 fractures along all or at least a portion of its circumscribing length to break open the assembly 20, and in particular, the handle 22. In addition, the bending motion of the handle 22 (i.e., distal end 30 relative to proximal end 28), and thereby the distal tip segment 58 of the applicator 26 relative to the proximal mounting segment 54, will also cause the median bending segment 56 of the applicator 26 to bend.

The distal end 30 of the handle 22 is moved away from the proximal end 28 and the applicator 26 along the length of the applicator 26 to uncover the distal tip segment 58 and tip 62 of the applicator 26. The median bending segment 56, having moved past its yield point during the bending motion of the handle 22, remains in its deformed, bent orientation (as shown in FIG. 4) after the distal end 30 is separated from the proximal end 28 of the handle 22. If the user is not satisfied with the resultant angular orientation, the distal end 30 may be temporarily replaced onto proximal end 28 of the handle 22 so that the user's fingers need not contact the tip 62 or the composition material 40 during additional bending movements, and contamination is prevented.

Optionally, the applicator assembly 20 may be opened without bending the applicator 26 in instances where a straight configuration of the applicator 26 is desired. To open the assembly 20 without bending the applicator 26, the distal end 30 of the handle 22 is twisted in an arc about its longitudinal axis while holding the proximal end 28 stationary. In order to shear apart the applicator assembly 20, the handle 22 is separated at weakened wall line 42.

Once the distal end 30 is removed from the proximal end 28 of the handle 22, the distal tip segment 58 of applicator 26 is uncovered and available for use. The composition material 40 adhered to the tip 62 of the applicator 26 is spread across a suitable surface. For example, in a dental material delivery system, the dental material on the tip 62 is applied to the desired tooth surface. Typically, the tip 62 of the applicator 26 bears a quantity of composition material 40 when the distal end 30 of the handle 22 is removed from the assembly 20 sufficient to complete the necessary procedure. If an additional amount of composition material 40 is desired, the applicator tip 62 is placed back in the distal end 30, and in particular the distal bore section 38, and into contact with the composition material 40 reservoir, or optional porous material. The tip 62 picks up additional composition material for use. As the applicator assembly 20 contains a single dose of composition material for a desired procedure, once the procedure is complete, the entire assembly 20 is discarded. The applicator assembly 20 has a length of about 125 mm to about 205 mm, whereas the length of the handle 22 and the applicator 26 with the distal end 30 removed is about 100 mm to about 130 mm. In addition, the distal end 30 has a length of about 20 mm to about 80 mm, whereas the cap 24 has a length of about 10 mm to about 15 mm.

A method for forming the material delivery system 20 includes molding the three main components, the handle 22, the cap 24 and the applicator 26, for example by injection molding. In addition, the tip 62 of the applicator 26 is processed to apply a tip material, such as bristles, fibers, open cell foam or the like. The applicator 26 is molded from a material that provides sufficient strength and stiffness to the resultant assembly during shipping, storage, handling and use including the acts of separating the handle 22 as described above. The selected material should also be compatible with the composition material 40 contained in the material delivery system 20 and provide satisfactory shelf life performance. Examples of a suitable material for the applicator 26 include a polyolefin, such as polyethylene or polypropylene.

Although polyethylene and polypropylene may be suitable materials for the applicator 26, they may not be suitable materials for the handle 22 and the cap 24 of the material delivery system 20. First, polyethylene and polypropylene may not provide a sufficient moisture barrier, thereby resulting in a shorter shelf life for the composition material 40 or resulting in contamination of the composition material 40, e.g., from moisture that might pass through the handle 22 and/or cap 24. Thus, a material delivery system that is comprised predominately of polyethylene or polypropylene is typically packaged in a foil pouch after manufacturing for transport and storage, which increases the overall cost of the material delivery system. Second, polyethylene and polypropylene may be too flexible to provide a clean break of the handle 22 at the weakened wall line 42 when the handle 22 is bent to uncover the applicator 26.

The handle 22 of material delivery system 20 may be preferably molded from a cyclic olefin copolymer, and in some embodiments of the material delivery system, the cap 24 is formed from a cyclic olefin copolymer. An example of a suitable cyclic olefin copolymer is TOPAS 8007 brand resin from Ticona (a business of Celanese AG, U.S. office in Summit, N.J.). Cyclic olefin copolymers provide sufficient strength and stiffness to the resultant assembly during shipping, storage, handling and use, including the act of separating the handle 22 as described above. Cyclic olefin copolymers also provide an effective high moisture barrier and effective oxygen permeability for the material delivery system 20 in which moisture is kept out of the assembly and oxygen is allowed through to the applicator 26 and the composition material 40. Forming the handle 22 and the cap 24 from a cyclic olefin copolymer provides a moisture barrier to prevent contamination of the applicator 26 and the composition material 40, thereby eliminating the requirement of an outer foil pouch without compromising the shelf-life of the assembly. In addition, cyclic olefin copolymers are stiffer than polyethylene and polypropylene, thereby providing a better, cleaner break at weakened wall line 42 when the handle 22 is bent and separated to access the applicator 26.

After the handle 22, the cap 24 and the applicator 26 are molded, the three components are assembled together to form the material delivery system 20. The applicator 26 is pressed into the distal open end 30 of the handle 22 under pressure to properly place the applicator 26 in the proximal tip retention segment 36. The proximal mounting segment 54 of the applicator 26 is inserted through the distal bore section 38 of the handle 22 and into the proximal tip retention section 36 of the bore 32.

The radial projections 60 located at the proximal segment 54 of the applicator 26 provide a nonremovable, fixed friction fit between the proximal segment 54 of the applicator 26 and the inner wall of the proximal bore section 36 of the handle 22. Sufficient pressure is required to create an interference fit between the applicator 26 and the handle 22. The friction fit and the radial projections 60 prevent the applicator 26 from separating from the handle 22 during separation of the handle 22 and/or use of the material delivery system 20. The applicator 26 is mechanically attached to the handle 22 at a point adjacent the proximal segment 54 thereof, which eliminates the need for additional bonding or welding processes used in current applicator assemblies. Because the handle 22 and the applicator 26 may be formed from dissimilar materials, the friction fit between the two components provides a nonremovable attachment that may be more difficult to or costly to achieve by other types of processing, e.g., bonding or welding the applicator 26 to the handle 22.

The median bending segment 56 of the applicator 26 is aligned with or distally from the radially extending weakened wall line 42 of the handle 22. The distal tip segment 58 of the applicator 26 extends into the distal section 38 of the handle bore 32. The length of the distal tip segment 58 can vary between different embodiments of the material delivery system 20, thus, the distal bore section 38 of the handle 22 is sized to accommodate varying applicator tip lengths, as well as a range of composition material volume.

The composition material 40 is introduced into the distal bore section 38 of the handle 22 through the distal open end 30. A pre-measured, desired volume of the composition material 40 fills the distal bore section 38 to provide a sufficient quantity for a single unit dose in the material delivery system 20.

The cap 24 is aligned over the distal open end 30 of the handle 22 and inserted into the distal section 38 of the bore 32. The handle 22 and the cap 24 are sealed together (for example, at radial extensions 48 and 50) to form a hermetic seal and retain the composition material 40 within the bore 32. Exemplary methods for sealing the assembly include ultrasonic sealing or welding, for example by ultrasonic energy from an ultrasonic horn. The longitudinal extension 52 of the cap 24 defines the available volume within the bore 32 for the composition material 40. Longitudinal extensions 52 of varying lengths are possible to accommodate the distal tip segment 58 length of the applicator 26 and the desired quantity of the composition material 40 within the bore 32. Varying the size of the longitudinal extension 52 of the cap 24 to adjust the available volume in the bore 32 may eliminate the additional manufacturing steps of changing the size of the handle 22 or the handle bore 32 to vary available volume.

After the applicator assembly 20 is sealed, it may be laser marked and packaged. The initially straight configuration of the applicator assembly 20 is an advantage during manufacturing, shipping and storage in that a large number of assemblies 20 can be packaged in a compact, tight array with little wasted space. The initially straight configuration of the assembly 20, in combination with the median bending segment 56, allows the user to bend the handle 22 to a user-selected angular orientation that is best suited for the procedure. In addition, the assembly 20 may be opened without bending the applicator 26 at the median bending segment 56 where the user desires keeping the applicator 26 in a straight configuration.

The applicator assemblies 20 described above are suitable for use with a wide variety of composition materials 40 for various dental, pharmaceutical and medical procedures. The composition material 40 could be a liquid, semi-liquid, gel, paste or powder. A particularly preferred composition is a one-part dental adhesive that cures upon exposure to light. An example of a suitable dental adhesive is SINGLE BOND brand adhesive from 3M Company, St. Paul, Minn. Other suitable compositions include dental etchants, sealants and primers. As used herein, the word "dental" includes all fields of dentistry including orthodontic and endodontic treatment.

Although the present invention has been described with reference to several embodiments, workers skilled in the art will recognize that changes may be made in form and detail without departing from the spirit and scope of the invention. A number of options and alternatives are possible to the applicator assemblies described above. For example, the handles described above could be provided with a flange or collar in order to assure that the composition does not drip onto the user's fingers when the applicator is held in an upward position during use.

The invention claimed is:

1. A method of forming a dental material storage container and dispenser, comprising:

molding an elongated handle, the handle formed to have a length, a proximal closed end, a distal open end, and a bore extending therein from the distal open end, with the bore having a tip retention section adjacent a proximal end thereof, and the handle having an annular weakened wall line along or distally from the tip retention section thereof;

molding a dental material applicator tip, the tip having a proximal mounting segment, a median bending segment and a distal applicator segment, the proximal segment having a plurality of projections radially projecting therefrom and being formed to be received within the tip retention section of the bore of the handle;

inserting the proximal segment of the applicator tip into the tip retention section of the bore through the distal open end, wherein the projections on the tip frictionally engage the bore to nonremoveably fixedly connect the tip to the handle, and wherein the median bending segment of the tip is aligned with or distally from the radially extending weakened wall line of the handle;

introducing a desired amount of dental material into the bore through the distal open end after inserting the proximal segment of the applicator tip into the tip retention section of the bore;

aligning a cap over the distal open end of the handle; and sealing the cap to the handle to retain the dental material in the bore.

2. The method of claim 1, and further comprising:

forming the cap to include a longitudinal extension thereon which extends proximally from the distal open end of the handle into the bore.

3. The method of claim 2, and further comprising:

adjusting an available volume in the bore for dental material by changing the size of the extension on the cap.

4. The method of claim 1, and further comprising:

forming outward radial extensions on one or both of the cap and handle adjacent the distal open end thereof.

5. The method of claim 1, wherein the handle has a distal portion which extends a sufficient extent distally from the weakened wall line to facilitate gripping thereof for bending the distal portion relative to a proximal portion of the handle.

6. The method of claim 1, wherein the sealing step includes ultrasonic sealing.

7. The method of claim 1 wherein the handle is formed from a cyclic olefin copolymer.

8. The method of claim 7 wherein the cap is formed from a cyclic olefin copolymer.

9. The method of claim 1 wherein the applicator is formed from a polyolefin.

10. The method of claim 9 wherein the applicator is formed from a polyethylene.

11. A dental material delivery system comprising:

an applicator having a proximal segment, a median bending segment and a distal tip segment;

an elongated handle having a proximal end and a distal end, the handle having a generally cylindrical bore extending proximally therein from the distal end within a surrounding wall of the handle, the bore having a proximal section with a proximal closed end and a distal section with a distal open end, and the wall having an annular weakened wall line disposed generally between the proximal and distal sections of the bore, wherein:

the proximal segment of the applicator is nonremoveably frictionally mounted within the proximal section of the bore proximate the proximal closed end, the median bending segment of the applicator is aligned generally longitudinally with the annular weakened wall line, and the distal tip segment of the applicator extends into the distal section of the bore towards the distal open end;

a desired amount of dental material disposed within the distal section of the bore;

a cap mounted to the handle adjacent the distal end thereof to seal off the distal open end of the distal section of the bore; and wherein the wall of the handle is separable at the annular weakened wall line to permit withdrawal of the distal tip segment of the applicator from the distal section of the bore and transfer of dental material borne by the distal tip segment from the bore to a patient's dental anatomy.

12. The dental material deilvery system of claim 11 wherein the proximal segment of the applicator has a plurality of radial projections thereon sized for interference fit with an inner diameter of the proximal section of the bore.

13. The dental material delivery system of claim 12 wherein each radial projection is a ring.

14. The dental material delivery system of claim 12 wherein each radial projection is an annular directional ribbing.

15. The dental material delivery system of claim 11 wherein the applicator is mounted in the bore whereby the flow of dental material proximally past the applicator into the proximal section of the bore is prevented.

16. The dental material delivery system of claim 11 wherein the handle is formed from a cyclic olefin copolymer.

17. The dental material delivery system of claim 16 wherein the cap is formed from a cyclic olefin copolymer.

18. The dental material delivery system of claim 11 wherein the applicator is formed from a polyolefin.

19. The dental material delivery system of claim 18 wherein the applicator is formed from a polyethylene.

20. The dental material delivery system of claim 11 wherein the elongated handle has a generally cylindrical shape, with at least two different outer diameter portions, a first distal portion extending distally from adjacent the bore proximal end having a first outer diameter, and a second proximal portion having a second outer diameter smaller than the first outer diameter.

21. The dental material delivery system of claim 11 wherein, adjacent its distal end, the handle has a radial extension thereon.

22. The dental material delivery system of claim 11 wherein the cap has a radial extension thereon.

23. The dental material delivery system of claim 11 wherein the cap has a longitudinal extension which extends proximally from the distal end of the handle, into the distal section of the bore.

24. The dental material delivery system of claim 23 wherein an available volume of the distal section of the bore for dental material is a function of the longitudinal extent of the longitudinal extension on the cap.

25. The dental material delivery system of claim 24 wherein the available volume is from about 100 microliters to about 500 microliters.

* * * * *

UNITED STATES PATENT AND TRADEMARK OFFICE
CERTIFICATE OF CORRECTION

| | |
|---|---|
| PATENT NO. | : 7,112,062 B2 |
| APPLICATION NO. | : 10/729221 |
| DATED | : September 26, 2006 |
| INVENTOR(S) | : Robert Lee |

It is certified that error appears in the above-identified patent and that said Letters Patent is hereby corrected as shown below:

<u>Column 4:</u>
Line 11, Delete "withing" and insert -- within --, therefor.

<u>Column 11:</u>
Line 20, In Claim 12, delete "deilvery" and insert -- delivery --, therefor.

Signed and Sealed this

Eighth Day of May, 2007

JON W. DUDAS
*Director of the United States Patent and Trademark Office*